(12) United States Patent
Betz et al.

(10) Patent No.: US 7,201,915 B2
(45) Date of Patent: Apr. 10, 2007

(54) POLYAMIDE STICK DISPENSING PRODUCT AND METHOD OF USE

(75) Inventors: Alison Betz, Middletown, NJ (US); Vikas M. Deshpande, Plainsboro, NJ (US); Wijnanda Hendrika van Kippersluis, Bussum (NL); Richard M. Boden, Ocean, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 269 days.

(21) Appl. No.: 10/683,525

(22) Filed: Oct. 10, 2003

(65) Prior Publication Data

US 2005/0079143 A1    Apr. 14, 2005

(51) Int. Cl.

| | |
|---|---|
| A61K 8/02 | (2006.01) |
| A61K 8/30 | (2006.01) |
| A61K 8/37 | (2006.01) |
| A61K 8/72 | (2006.01) |
| A61K 8/88 | (2006.01) |
| A45D 40/00 | (2006.01) |
| A61Q 13/00 | (2006.01) |
| A01N 25/08 | (2006.01) |
| A01N 25/10 | (2006.01) |
| A01N 25/34 | (2006.01) |
| A01N 65/00 | (2006.01) |
| A01N 61/00 | (2006.01) |
| A01N 59/00 | (2006.01) |
| A01N 57/00 | (2006.01) |
| A01N 55/00 | (2006.01) |
| A01N 53/00 | (2006.01) |
| A01N 51/00 | (2006.01) |
| A01N 49/00 | (2006.01) |
| A01N 47/00 | (2006.01) |
| A01N 45/00 | (2006.01) |
| A01N 43/00 | (2006.01) |
| A01N 41/00 | (2006.01) |
| A01N 39/00 | (2006.01) |
| A01N 37/00 | (2006.01) |
| A01N 35/00 | (2006.01) |
| A01N 33/00 | (2006.01) |
| A01N 31/00 | (2006.01) |
| A01N 29/00 | (2006.01) |
| A01N 27/00 | (2006.01) |

(52) U.S. Cl. .................. 424/401; 514/918; 514/919; 514/772.3; 424/10.31; 424/84; 424/DIG. 10

(58) Field of Classification Search .............. 424/401, 424/84, 10.31, DIG. 10; 514/772.3, 919, 514/918

See application file for complete search history.

(56) References Cited

U.S. PATENT DOCUMENTS

| 4,009,253 A | 2/1977 | Schleppnik et al. |
|---|---|---|
| 4,187,251 A | 2/1980 | Schleppnik |
| 4,310,512 A | 1/1982 | Schleppnik |
| 4,534,891 A | 8/1985 | Boden et al. |
| 4,622,221 A | 11/1986 | Schleppnik |
| 4,719,105 A | 1/1988 | Schleppnik |
| 4,968,496 A | 11/1990 | Rohe et al. |
| 5,229,126 A | 7/1993 | Anderson et al. |
| 5,275,496 A | 1/1994 | Fattori et al. |
| 5,302,377 A | 4/1994 | Pereira et al. |
| 5,409,958 A | 4/1995 | Butler et al. |
| 5,439,941 A | 8/1995 | Butler et al. |
| 5,441,988 A | 8/1995 | Butler et al. |
| 5,455,025 A | 10/1995 | Pereira et al. |
| 5,501,805 A | 3/1996 | Behan et al. |
| 5,508,417 A | 4/1996 | Osei-Gyimah et al. |
| 5,540,853 A | 7/1996 | Trinh et al. |
| 5,554,588 A | 9/1996 | Behan et al. |
| 5,576,011 A | 11/1996 | Butler et al. |

(Continued)

FOREIGN PATENT DOCUMENTS

DE    EP 1319704 A1    12/2002

(Continued)

Primary Examiner—Sreeni Padmanabhan
Assistant Examiner—James H. Alstrum-Acevedo
(74) Attorney, Agent, or Firm—Elizabeth M Quirk; Joseph F. Leightner

(57) ABSTRACT

Described for the purpose of application to an inanimate laminar substantially solid surface is a substantially hydrocarbon-free functional substance-providing stick article having consistently-maintained functional composition integrity comprising a stiff, substantially monophasic, thermally-reversible hydrocarbon-free composition consisting essentially of a mixture of:
(a) a structural support polymer containing an ester-terminated polyamide and/or at least one tertiary amide-terminated polyamide;
(b) a high concentration of a system-compatible functional composition which is one or more of a perfume composition, an insect repellant composition, an animal repellant composition, an anti-microbial composition, an insect attractant composition and/or an air freshener composition; and
(c) at least one compatible operativeness organic acid ester and/or metal salt additive which enables the stick, prior to, during and subsequent to application thereof to the inanimate laminar substantially solid surface, to have retained stiffness, pliability, durability, consistency, lack of tackiness, and a relatively high degree of glide, and to cause the inanimate laminar substantially solid surface to which the stick is applied to have a high degree of surface rinsability immediately subsequent to application of the stick.

Also described is a package for conveniently handling and utilizing the stick article.

3 Claims, 4 Drawing Sheets

U.S. PATENT DOCUMENTS

| | | | |
|---|---|---|---|
| 5,597,555 A | 1/1997 | Pereira et al. |
| 5,633,236 A | 5/1997 | Warren et al. |
| 5,676,163 A | 10/1997 | Behan et al. |
| 5,683,687 A | 11/1997 | Marin et al. |
| 5,753,686 A | 5/1998 | Marin et al. |
| 5,770,189 A | 6/1998 | Airey et al. |
| 5,783,657 A | 7/1998 | Pavlin et al. |
| 5,990,244 A | 11/1999 | Warakomski et al. |
| 5,998,570 A | 12/1999 | Pavlin et al. |
| 6,111,055 A | 8/2000 | Berger et al. |
| 6,169,160 B1 | 1/2001 | MacQueen et al. |
| 6,207,679 B1 | 3/2001 | Cuny et al. |
| 6,214,063 B1 | 4/2001 | DeStefano et al. |
| 6,242,509 B1 | 6/2001 | Berger et al. |
| 6,268,466 B1 | 7/2001 | MacQueen et al. |
| 6,386,778 B1 | 5/2002 | Guay et al. |
| 6,402,408 B1 | 6/2002 | Ferrari |
| 6,432,891 B1 | 8/2002 | O'Connor |
| 6,439,880 B1 | 8/2002 | Ray |
| 6,451,065 B2 | 9/2002 | Trinh et al. |
| 6,469,131 B2 | 10/2002 | Lawson et al. |
| 6,495,512 B1 | 12/2002 | White et al. |
| 6,517,759 B1 | 2/2003 | Ferenc et al. |
| 6,544,302 B2 | 4/2003 | Berger et al. |
| 6,551,365 B2 | 4/2003 | Berger et al. |
| 6,551,998 B1 | 4/2003 | Spatola et al. |
| 6,592,857 B2 | 7/2003 | Lawson et al. |
| 2001/0002962 A1 | 6/2001 | Baines et al. |
| 2002/0019510 A1 | 2/2002 | Orth et al. |
| 2002/0035237 A1 | 3/2002 | Lawson et al. |
| 2002/0055562 A1* | 5/2002 | Butuc .......................... 524/80 |
| 2002/0127192 A1* | 9/2002 | Murphy et al. ................ 424/64 |
| 2003/0007945 A1 | 1/2003 | Arif et al. |
| 2003/0110682 A1 | 6/2003 | Williams et al. |
| 2003/0114520 A1 | 6/2003 | Pereira et al. |
| 2003/0166496 A1* | 9/2003 | Godfroid et al. ........... 510/503 |
| 2003/0223943 A1 | 12/2003 | Uang et al. |

FOREIGN PATENT DOCUMENTS

| | | |
|---|---|---|
| GB | 2372447 | 8/2002 |
| GB | 2372448 | 8/2002 |
| GB | 2372449 | 8/2002 |
| GB | 2372450 | 8/2002 |
| WO | WO 93/05678 | 4/1993 |
| WO | WO 00/40216 | 7/2000 |
| WO | WO 02/47626 A1 | 6/2002 |
| WO | WO 02/058642 A2 | 8/2002 |
| WO | WO 02/066084 | 8/2002 |
| WO | WO 02/092663 A1 | 11/2002 |
| WO | WO 02/102322 A2 | 12/2002 |
| WO | WO 03/074642 A1 | 9/2003 |

\* cited by examiner

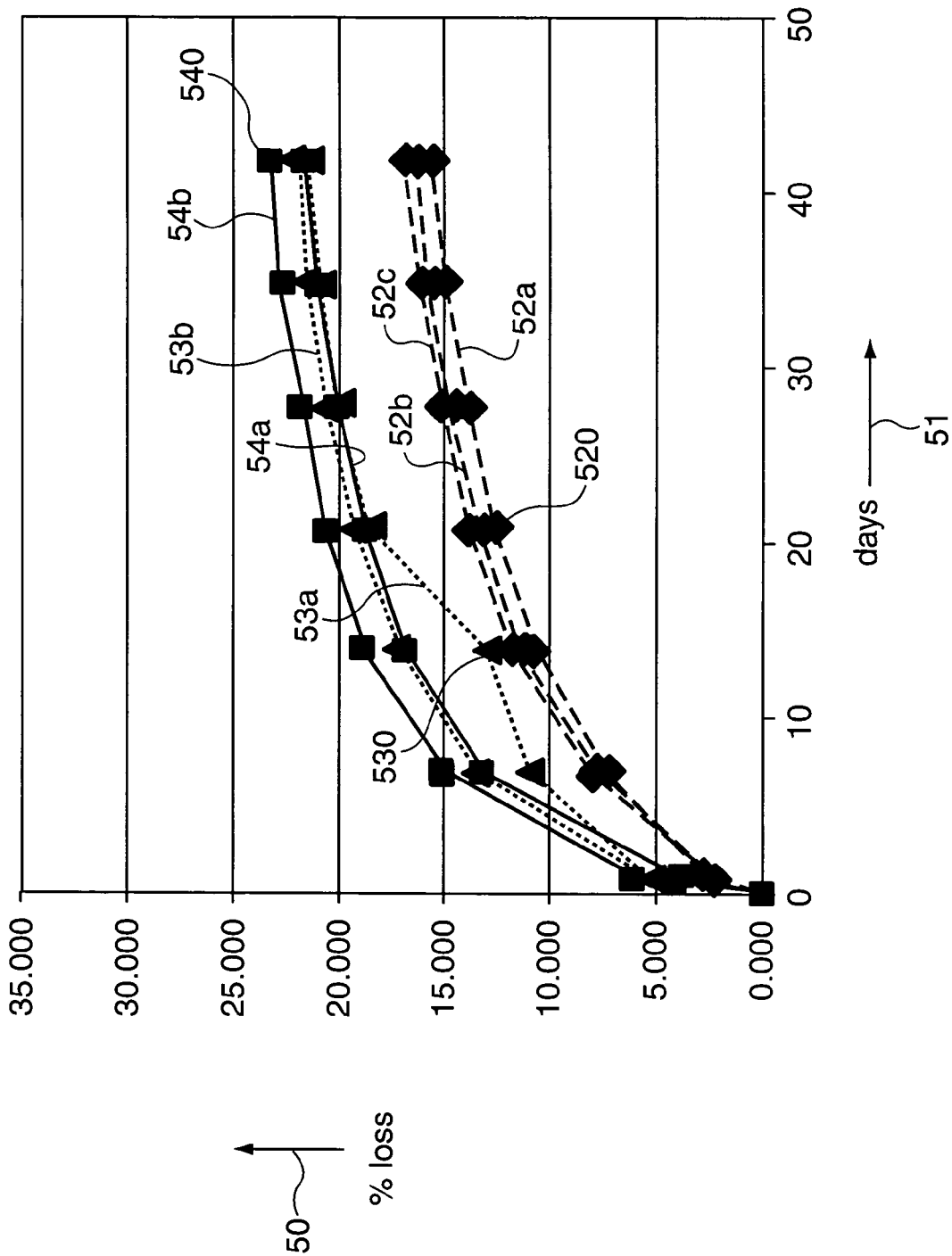

POLYAMIDE STICK DISPENSING PRODUCT AND METHOD OF USE

FIELD OF THE INVENTION

Ester-terminated and tertiary amide-terminated polyamide stick articles which are substantially hydrocarbon-free and which contain high concentrations of functional substances, such as fragrances and air freshener compositions. The articles are useful for providing the functional substances to a surface by means of rubbing the stick article onto the surface.

BACKGROUND OF THE INVENTION

The prior art contains several references to functional substance-providing stick articles, for example (a) tertiary amide-terminated polyamide polyglyceryl-2 polyhydroxystearate pigment-containing sticks for lipstick applicators described in U.S. Pat. No. 6,469,131; (b) tertiary amide-terminated polyamide-salicylic acid octyl monoester-linoleic acid isostearyl monoester-mineral oil sunblock stick articles containing 0.60% fragrance described in Example 7 of U.S. Pat. No. 6,592,857; and (c) ester-terminated polyamide-mineral oil-functional ingredient stick applicators including fragrance and insect repellent applicators as described in U.S. Pat. No. 6,111,055.

Nevertheless, such references are either directed to polyamide stick articles having very low concentrations of functional ingredient in the scope of our invention, e.g., fragrance, or polyamide stick articles containing high concentrations of undesirable hydrocarbons, e.g., mineral oil. Thus, no teaching exists in the prior art of functional ingredient-providing hydrocarbon-free polyamide stick articles, or dispensing packages containing and employing such stick articles. Furthermore, no teaching exists in the prior art of the inclusion of such articles in dispensing-type packages where such article-containing packages are deployed for coating functional substance-containing and emitting films on inanimate solid laminar surfaces.

SUMMARY OF THE INVENTION

Our invention is directed to a substantially hydrocarbon-free functional substance-providing stick article having consistently-maintained functional composition and dimensional integrity comprising a stiff, substantially monophasic, thermally-reversible composition comprising:

(a) a structural support polyamide polymer selected form one ester-terminated polyamide and tertiary amide-terminated polyamide;

(b) a system-compatible functional composition which is one or more of a perfume composition, an insect repellant composition, an animal repellant composition, an anti-microbial composition, an insect attractant composition and/or an air freshener composition; and (c) at least one compatible additive having a molecular weight of from about 350 to about 1500 which is at least one of the group of esters of mono-, di- and tri-carboxylic acids, esters of alkoxylated mono-, di- and tri-carboxylic acids, metal salts of hydroxy-mono-, di- and tri-carboxylic acids, metal salts of di- and tri-carboxylic acid partial esters, metal salts of alkoxylated mono-, di- and tri-carboxylic acids, metal salts of alkoxylated di- and tri-carboxylic acid partial esters and solutions thereof, optionally in admixture with one or more sodium salts of a $C_{12}$–$C_{18}$ saturated or unsaturated carboxylic acid;

with the provisos that the weight ratio range of structural support polymer:system-compatible functional composition is from about 90:10 to about 55:45 and the weight percent of operativeness additive is from about 0.2% to about 10% by weight of the functional substance-providing stick article.

In a preferred embodiment the compatible additive causes the stick article to have an operative value V of between 7 and 10 on a scale of 1–10 as measured by the "IFF SPDC Test" ("Substance-Providing Dimensional Compatibility Test" as described herein.

Our invention is further directed to a package for utilization of the above-mentioned functional substance-providing stick article comprising means for supporting said functional substance-providing stick article such that an end portion of said stick article can be exposed for use. The means for supporting said stick article include a container for surrounding the stick article, the container having an opening such that the stick article can be exposed for use, and a border of the stick-surrounding member forming the opening, said border forming a top end of the supporting means, such that said end portion can be elevated from said means for supporting and can protrude therefrom so as to be exposed for use, said stick article being contained within said stick-surrounding member.

Our invention is still further directed to a process for applying a controllably releasable functional substance which is one or more of a perfume composition, an insect repellant composition, a malodor control agent, an animal repellant composition, an anti-microbial composition, an insect attractant composition and/or an air freshener composition to an inanimate substantially solid surface, preferably a laminar surface comprising the steps of providing the above mentioned package; exposing for use the end portion of said stick article contained within said package; providing an solid surface to be treated; and applying the end portion of said stick article contained within said package to a finite area of said solid surface.

BRIEF DESCRIPTION OF THE DRAWINGS

FIG. 5 is a graphical representation of a second series of curves for three different temperatures: 70° F., 110° F. and 120° F. showing time in days (on the 'x' axis) vs. % weight loss of fragrance B-containing stick article of our invention contained in the package as illustrated in FIG. 3 onto an inanimate solid laminar surface. Fragrance B is described in Example B, infra. The stick article tested is that of Example IB, infra.

DETAILED DESCRIPTION OF THE INVENTION

Figure 1:
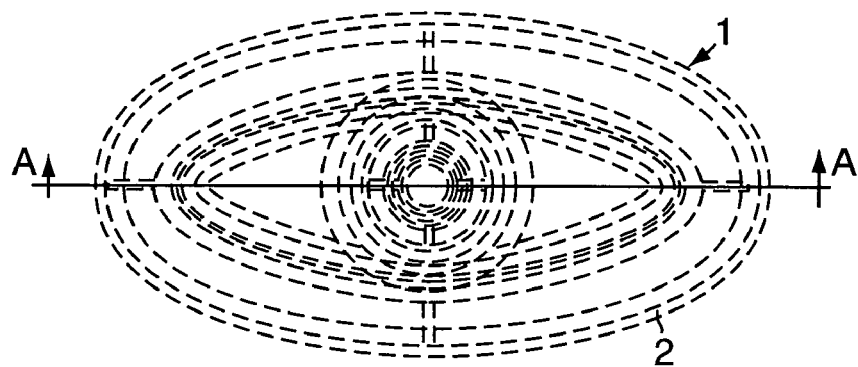
FIG. 1 is a top view of a package useful for containing the stick article of our invention and for carrying out the process of applying the stick article of our invention to an inanimate solid laminar surface whereat the functional product contained in the stick article of our invention is emitted via a controlled release mechanism.

The term "substantially hydrocarbon-free" is intended herein to mean that the concentration of any hydrocarbon in the stick article of our invention, e.g., mineral oil, is less than 1% of the weight of the stick article of our invention; preferably less than 0.5% by weight of the stick article of our invention; and more preferably less than 0.1% by weight of the stick article of our invention.

The term "system-compatible functional composition" is herein intended to mean functional compositions, for example, fragrance compositions which, when made part of the support polymer-operativeness additive system do not compromise the transparency of the stick article by causing haze or cloudiness, due to, for example, phase separation or synerisis to occur as a result of the composition being admixed with the support polymer-operativeness additive system.

The term "consistently-maintained functional composition and dimensional integrity" is intended herein to mean that when the stick article of our invention is in use in applying a film to an inanimate solid laminar surface, the proportions of the constituents and the chemical properties of the functional composition, e.g., the fragrance composition that is evolved into the environment on use of the stick article of our invention are substantially identical to the proportions and chemical properties of the constituents originally present in the stick article and originally admixed with the support polymer-operativeness additive system; and the geometric dimensions thereof with reference to the "x", "y" and "z" axes on use thereof are substantially identical to the geometric dimensions originally existent in the stick article.

The term, "stiff" is herein intended to mean that the stick article of our invention is self-supporting and non-flowable at ambient temperatures or less and at ambient pressures, e.g., at temperatures of less than or about equal to 35° C. and at pressures of about 1 atmosphere absolute.

The term "monophasic" is herein intended to mean that the stick article of our invention on use or when not in use exists in one unitary phase without any phase separation resulting from the inclusion in the support polymer-operativeness additive system of a functional composition, e.g., a fragrance composition.

The term "thermally reversible" is herein intended to mean that the stick article of our invention retains the original proportions of the constituents of its composition and retains its original physical characteristics and original dimensions on use thereof, and subsequent to use thereof.

The term: "IFF SPDC Test" for "Substance-Providing Dimensional Compatibility Test", is intended herein to mean the determination of an operative value V of the stick article of our invention measured according to the algorithm:

$$V = V_1\sigma + V_2\lambda + V_3\delta + V_4\kappa + V_5\tau + V_6\gamma + V_7\rho$$

wherein $\sigma$ is the degree of stiffness of the stick, as measured on a scale of 1–10, with $V_1$ being the fraction indicating the priority of the degree of stiffness, with $0.05 \leq V_1 \leq 0.25$; $\lambda$ is the measure of pliability of the stick, as measured on a scale of 1–10, with $V_2$ being the fraction indicating the priority of the degree of pliability, with $0.05 \leq V_2 \leq 0.25$; $\delta$ is the measure of durability of the stick, as measured on a scale of 1–10, with $V_3$ being the fraction indicating the priority of the degree of durability, with $0.05 \leq V_3 \leq 0.25$; $\kappa$ is the measure of the consistency of the stick, as measured on a scale of 1–10, with $V_4$ being the fraction indicating the priority of the degree of consistency of the stick, with $0.05 \leq V_4 \leq 0.25$; $\tau$ is the measure of the lack of tackiness of the stick, as measured on a scale of 1–10 with a value of '10' indicating '0' tackiness, with $V_5$ being the fraction indicating the priority of the degree of lack of tackiness, with $0.05 \leq V_5 \leq 0.25$; $\gamma$ is the measure of the degree of glide of the stick, on use, as measured on a scale of 1–10 with $V_6$ being the fraction indicating the priority of the degree of glide of the stick, on use, with $0.05 \leq V_6 \leq 0.25$; and $\rho$ is the measure of surface rinsability immediately after use of the stick with $V_7$ being the fraction indicating the priority of the degree of surface rinsability immediately after use of the stick, with $0.05 \leq V_7 \leq 0.25$, wherein $\Sigma V_i = 1$. A result range of $6 \leq V \leq 10$ is a desired result for the operativeness of the stick articles of our invention. A result range of $7.5 \leq V \leq 10$ is a more preferred result for the operativeness of the stick articles of our invention. A result range of $9 \leq V \leq 10$ is a most preferred result for the operativeness of the stick articles, and hence the most preferred desirable result of the IFF SPDC Test for the stick articles of our invention.

Preferable ester-terminated polyamides useful in the practice of our invention are those disclosed in Pavlin et al., U.S. Pat. No. 5,998,570 the disclosure of which is herein incorporated by reference, and include those ester-terminated polyamides prepared by reacting "x" equivalents of a dicarboxylic acid wherein at least 50% of those equivalents are from polymerized fatty acid, "y" equivalents of ethylenediamine and "z" equivalents of an alcohol which is in the alternative, or in combination cetyl alcohol and/or stearyl alcohol wherein:

$$0.9 \leq \frac{x}{y+z} \leq 1.1 \text{ and } 0.1 \leq \frac{z}{y+z} \leq 0.7.$$

More preferably, the ester-terminated polyamide is one of a group having a weight-average molecular weight of about 6000 and a softening point in the range of from 88° C. to 94° C. prepared by reacting "x" equivalents of $C_{36}$ dicarboxylic acid, "y" equivalents of ethylenediamine and "z" equivalents of an alcohol which is, in the alternative or in combination cetyl alcohol and/or stearyl alcohol wherein $$0.9 \leq \frac{x}{y+z} \leq 1.1 \text{ and } 0.1 \leq \frac{z}{y+z} \leq 0.7.$$

Most preferable are the mineral oil-free ester terminated polyamiides, SYLVACLEAR 100LM, UNICLEAR 100 and UNICLEAR 100V, registered trademarks of the Arizona Chemical Company of Panama City, Fla.

Preferable tertiary amide-terminated polyamides useful in the practice of our invention are those disclosed in MacQueen et al., U.S. Pat. No. 6,268,466 issued on Jul. 31, 2001, the specification of which is herein incorporated by reference, and include those tertiary amide-terminated polyamides prepared by reacting "x" equivalents of dicarboxylic acid wherein at least 50% of those equivalents are from polymerized fatty acid, "y" equivalents of ethylenediamine and "z" equivalents of a monofunctional reactant having a secondary amine group as the only reactive functionality wherein $$0.9 \leq \frac{x}{y+z} \leq 1.1 \text{ and } 0.1 \leq \frac{z}{y+z} \leq 0.7.$$

Most preferable are those tertiary amide-terminated polyamides disclosed in Example I of U.S. Pat. No. 6,268,466.

The compatible operativeness additive, as stated supra may be at least one of the group of esters of mono-, di- and tri-carboxylic acids, esters of alkoxylated mono-, di- and tri-carboxylic acids, metal salts of hydroxy-mono-, di- and tri-carboxylic acids, metal salts of di- and tri-carboxylic acid partial esters, metal salts of alkoxylated mono-, di- and tri-carboxylic acids, metal salts of alkoxylated di- and tri-carboxylic acid partial esters and solutions thereof having a molecular weight in the range of from about 350 to about 1500, optionally in admixture with one or more sodium salts of a $C_{12}$–$C_{18}$ saturated or unsaturated carboxylic acid.

Examples of preferred operativeness additives which are esters of alkoxylated mono-, di- and tri-carboxylic acids useful in the practice of our invention are set forth in U.S. Pat. Nos. 5,302,377, 5,455,025, 5,597,555 and Published U.S. Patent Application U.S. 2003/0114520 A1 published on Jun. 19, 2003, for example, the tri-n-propoxy diester of myristyl alcohol and adipic acid (Di-PPG-3-myristyl adipate). A more preferred class of such esters are fatty alkoxylate esters which are diesters of an aliphatic or aromatic dicarboxylic acid formed by reacting said acid with a stoichiometric excess of one or more polyalkoxylated fatty alcohols, the fatty moieties of which contain from 12 to 22 carbon atoms.

A preferred operativeness additive is a metal salt of a hydroxy-carboxylic acid useful in the practice of our invention, zinc ricinoleate (the zinc salt of 12-hydroxy-9-octadecenoic acid) is set forth in U.S. Pat. No. 4,968,496 and Published Application for U.S. Letters Patent U.S. 2003/0007945 A1 published on Jan. 9, 2003. It is a highly preferred embodiment of the invention, the zinc ricinoleate is used in combination with one or more 1-hydroxy-2-ethoxyethyl ethers of $C_{12}$–$C_{14}$ alcohols in a ratio range of from about 1:1.5 to about 1.5:1 by weight.

The following Table I indicates a number of most preferred operativeness additives taken alone or in combination with one or more sodium salts of a $C_{12}$–$C_{18}$ saturated or unsaturated carboxylic acid and their respective ranges of usage in the stick article of our invention:

As stated supra, the functional products contained in the stick article of our invention include without limitation fragrances, antimicrobial substances, animal repellents, malodor treatment, insect attractants, and insect repellents. The functional products preferably have a C $\log_{10}$P in the range of from about 1 to about 6.5, without restriction on the molecular weight of each of said components wherein P is the n-octanol/water partition coefficient of the fragrance component. The concentration range of the functional product in the stick article of our invention is preferably from about 10% to about 45% by weight of the stick article of our invention.

The following functional products are provided as examples of the types of materials that can be incorporated in the present invention. Those with skill in the art will readily be able to use the described materials as well as various combinations of materials as well as other materials not provided herein without departing from the scope of the present invention. Suitable fragrance chemicals are found in for example U.S. Pat. Nos. 4,534,891, 5,501 805, 5,554,588, and 5,676,163. Another source of suitable fragrances is found in *Perfumes, Cosmetics and Soaps,* Second Edition, edited by W. A. Poucher, 1959. Examples of fragrance with anti-microbial properties useful in the present invention are set forth in U.S. Pat. Nos. 6,495,512 and 6,517,759. Suitable insect repellant materials include the materials disclosed in U.S. Pat. Nos. 5,441,988, 5,576,011, 5,409,958, 5,439,941, 5,683,687, 5,753,686, and 5,633,236. Suitable malodor treating substances are described in U.S. Pat. Nos. 4,009, 253, 4,187,251, 4,310,512, 4,622,221, 4,719,105 and 6,432, 891. Suitable insect attractant materials are found in U.S. Pat. Nos. 5,770,189, 5,990,244, 5,229,126 and malodor agents 6,551,998, 6,207,679, and 5,508,417.

The values of C $\log_{10}$P of many functional product ingredients, for example, fragrance ingredients and/or anti-microbial ingredients, contained in personal treatment compositions and/or cosmetic compositions is discussed in published U.S. Patent Application US 2003/0110682 A1 published on Jun. 19, 2003, U.S. Pat. Nos. 5,540,853 and 6,451,065. Furthermore, values of $\log_{10}$P have been reported; for example, the Pomona92 database, available from Daylight Chemical Information Systems, Inc., Daylight CIS, Irvine, Calif. However, the $\log_{10}$P values are most conveniently calculated by the "CLOGP" program, also available from Daylight CIS. This program also lists experimental $\log_{10}$P values when they are available in the

TABLE I

| Generic Name | Trade Name | Range of Usage |
|---|---|---|
| Zinc Ricinoleate (50%) + mixture of 1-hydroxy-2-ethoxyethyl ethers of $C_{12}$–$C_{14}$ alcohols (50%) | TEGO Sorb Conc. 50 (from Goldschmidt A. G., Germany) | 1–10% by weight of stick article |
| Mixture of octyl stearate, octyl palmitate and dioctyl adipate | WICKENOL-163 (WICKENOL from Caschem, Inc., Bayonne, New Jersey) | 0.2–0.8% by weight of stick article |
| Tripropoxy diester of myristyl alcohol and adipic acid (di-PPG-3-myristyl adipate) | CROMOLLIENT DP3-A (CROMOLLIENT from Croda International plc, U.K.) | 0.2–0.8% by weight of stick article |
| Mixture of sodium stearate and tripropoxy diester of myristyl alcohol and adipic acid (di-PPG-3-myristyl adipate) in weight ratio range of 1:1 to 4:1 sodium stearate:diester | Mixture of CROMOLLIENT DP3-A and Sodium Stearate C-1 CK WITCO (Witco Corporation of New York, N.Y., U.S.A.) | 1.5–3.0% by weight of stick article |

Pomona92 database. The "calculated $\log_{10}P$" (C $\log_{10}P$) is determined by the Hansch and Leo "fragment" approach based on the chemical structure of each perfume ingredient, and takes into account the numbers and types of atoms, the atom connectivity and the chemical bonding. The C $\log_{10}P$ values which are the most reliable and widely used estimates for this physicochemical property, are preferably used instead of the experimental $\log_{10}P$ values for the selection of functional ingredients, including perfume ingredients which are useful in the stick articles of our invention.

Specific examples of preferred fragrance components useful in the stick articles of our invention, and the molecular weights and C $\log_{10}P$ values of each of said components are set forth in Table II below.

TABLE II

| Fragance Component | Clog$_{10}$P value | Molecular Weight |
| --- | --- | --- |
| benzaldehyde | 1.480 | 106.12 |
| benzyl acetate | 1.960 | 150.17 |
| laevo-carvone | 2.083 | 150.22 |
| geraniol | 2.649 | 154.26 |
| cis-jasmone | 2.712 | 164.25 |
| β-phenylethyl alcohol | 1.183 | 122.17 |
| α-terpineol | 2.569 | 154.25 |
| δ-nonalactone | 2.760 | 156.23 |
| nerol | 2.649 | 154.25 |
| iso-eugenol | 2.547 | 164.21 |
| amyl salicylate | 4.601 | 208.26 |
| benzyl salicylate | 4.383 | 228.25 |
| β-caryophyllene | 6.333 | 204.36 |
| cedrol | 4.530 | 222.37 |
| ethyl undecylenate | 4.888 | 212.34 |
| geranyl anthranilate | 4.216 | 273.38 |
| α-irone | 3.820 | 206.33 |
| phenyl ethyl benzoate | 4.058 | 226.28 |
| phenylethyl phenyl acetate | 3.767 | 240.31 |
| 5-acetyl-1,1,2,3,3,6-hexamethyl indane | 5.977 | 258.41 |
| cyclopentadecanolide | 6.246 | 240.39 |
| d-limonene | 4.232 | 136.24 |
| cis-p-t-butylcyclohexyl acetate | 4.019 | 198.31 |
| amyl cinnamic aldehyde | 4.324 | 202.30 |
| benzaldehyde | 1.480 | 106.12 |
| benzyl acetate | 1.960 | 150.17 |
| laevo-carvone | 2.083 | 150.22 |
| geraniol | 2.649 | 154.26 |
| cis-jasmone | 2.712 | 164.25 |
| β-phenylethyl alcohol | 1.183 | 122.17 |
| α-terpineol | 2.569 | 154.25 |
| δ-nonalactone | 2.760 | 156.23 |
| dihydromyrcenol | 3.03 | 156.27 |
| δ-undecalactone | 3.830 | 184.28 |
| amyl cinnamate | 3.771 | 218.30 |
| benzophenone | 3.120 | 182.22 |
| α-irone | 3.820 | 206.33 |
| nerol | 2.649 | 154.25 |
| 2-methoxynaphthalene | 3.235 | 158.20 |
| musk ketone | 3.014 | 294.30 |
| musk tibetine | 3.831 | 266.30 |
| myristicin | 3.200 | 192.22 |
| 6-phenyl heptanol-2 | 3.478 | 193.30 |
| 1-phenyl hexanol-5 | 3.299 | 178.28 |
| α-santalol | 3.800 | 220.36 |
| iso-eugenol | 2.547 | 164.21 |
| amyl salicylate | 4.601 | 208.26 |
| benzyl salicylate | 4.383 | 228.25 |
| β-caryophyllene | 6.333 | 204.36 |
| cedrol | 4.530 | 222.37 |
| cedryl acetate | 5.436 | 264.41 |
| cedryl formate | 5.070 | 238.37 |
| cyclohexyl salicylate | 5.265 | 220.29 |
| γ-dodecalactone | 4.359 | 198.31 |
| ethyl undecylenate | 4.888 | 212.34 |
| geranyl anthranilate | 4.216 | 273.38 |
| β-phenylethyl benzoate | 4.058 | 226.38 |
| β-phenylethyl phenyl acetate | 3.767 | 240.31 |

TABLE II-continued

| Fragance Component | Clog$_{10}$P value | Molecular Weight |
| --- | --- | --- |
| 5-acetyl-1,1,2,3,3,6-hexamethyl indane | 5.977 | 258.41 |
| cyclopentadecanolide | 6.246 | 240.39 |
| d-limonene | 4.232 | 136.24 |
| cis-p-t-butylcyclohexyl acetate | 4.019 | 198.31 |
| amyl cinnamic aldehyde | 4.324 | 202.30 |
| linalyl benzoate | 5.233 | 258.36 |

Figure 2:
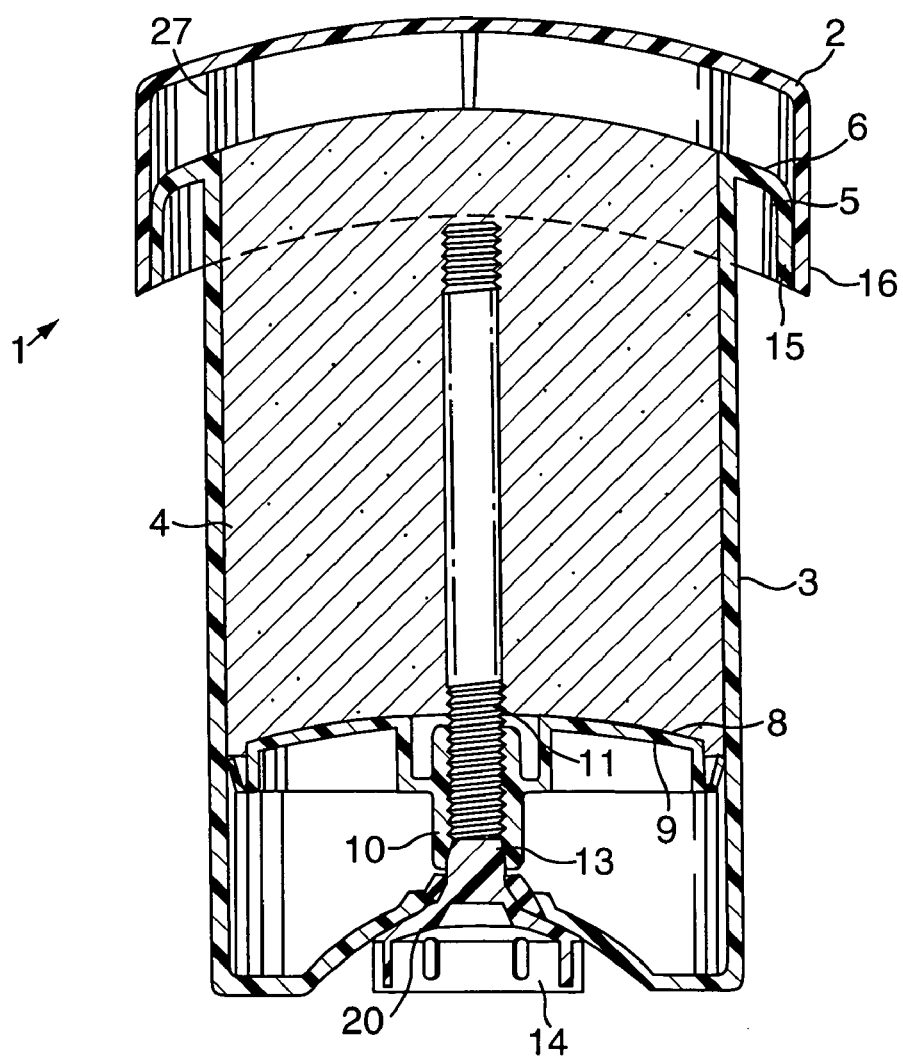
FIG. 2 is a cut-away side elevation view of the package of FIG. 1.
Figure 3:
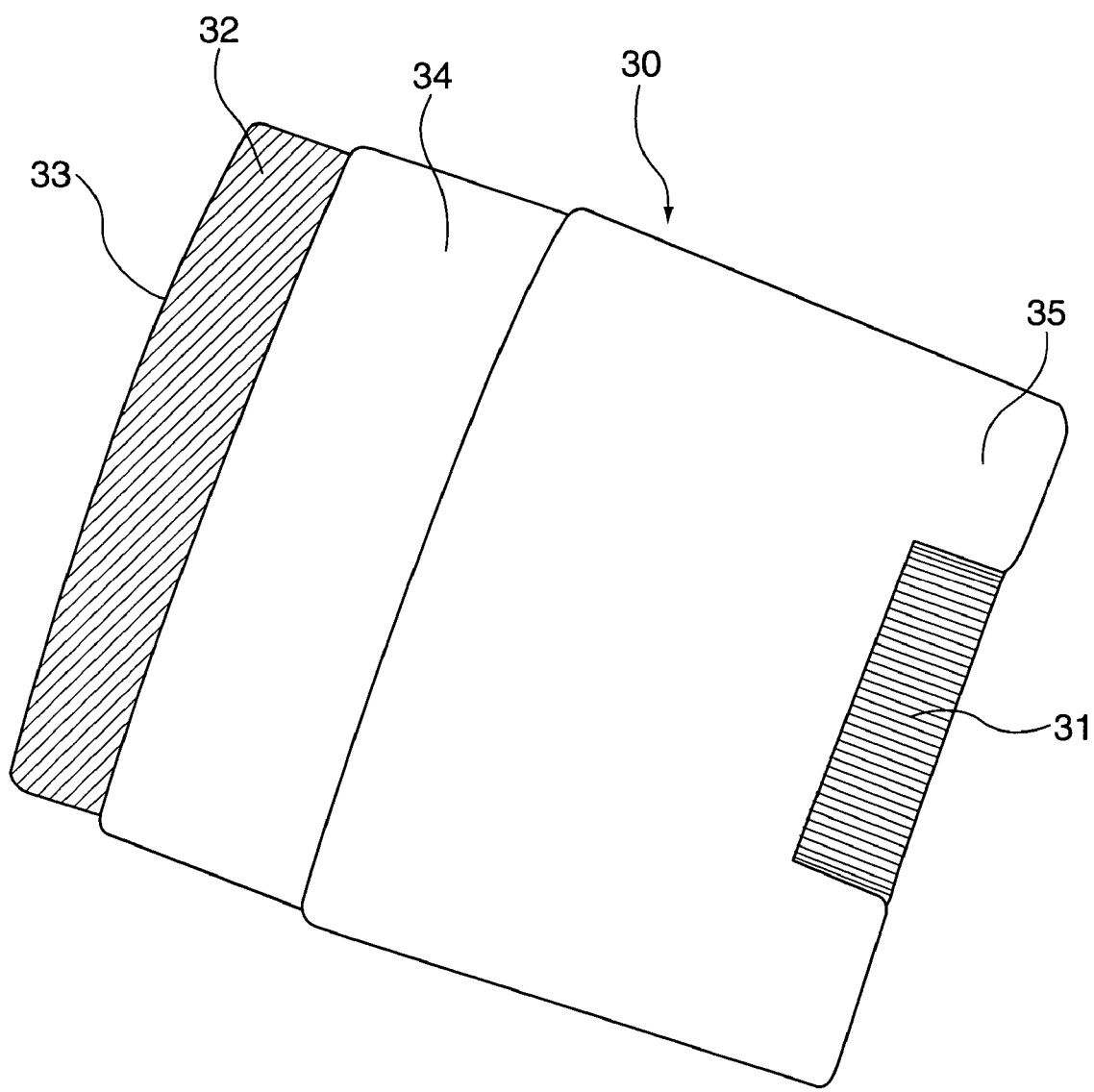
FIG. 3 is a perspective view of a second embodiment of the package of our invention showing the exposed stick article of our invention contained therein and ready for use.

The stick articles of our invention, when used in a preferred manner in the practice of our invention are contained, for example, in a package as illustrated in FIGS. 1, 2 and 3 described infra. Packages which are so useful in the practice of our invention are described in detail in U.S. Pat. Nos. 5,275,496 and 6,386,778 and Published U.S. Patent Application US 2001/0002962 A1 published on Jun. 7, 2001.

The stick article of our invention comprise means for supporting the functional substance-providing stick article of our invention such that an end portion of said stick article can be exposed for use, with the means for supporting said stick article including a stick-surrounding member for surrounding the stick article, the stick-surrounding member having an opening such that the stick article can be exposed for use, and a border of the stick-surrounding member forming the opening, said border forming a top end of the supporting means, such that said end portion can be elevated from said means for supporting and can protrude therefrom so as to be exposed for use, said stick article being contained within said stick-surrounding member. For example, the means for elevating includes a screw feed mechanism having an elevator screw such that upon rotation of the elevator screw the stick article is pushed up from the bottom such that the end portion protrudes and is exposed for use. As a second example, the means for elevating is a means for pushing up the stick article so that the end portion protrudes from the means for supporting and is exposed for use.

The present invention also provides a process for applying a controllably releasable functional substance such as a perfume composition, an insect repellant composition, a malodor treating material, an animal repellant composition, an anti-microbial composition, an insect attractant composition and/or an air freshener composition to a surface, preferably an inanimate laminar substantially solid surface. The process comprising the steps of providing a package as described above; exposing for use the end portion of said stick article contained within said package; providing surface to be treated; and applying the end portion of said stick article contained within said package to the surface. The present invention has the advantage of being able to deliver the functional ingredients directly to a surface, while not depositing a greasy or unsightly or staining residue. The present invention allows the functional materials to be directly deposited to a countertop, refuse container, wall, litter box or any other location where it would be desirable to provide a pleasant fragrance, anti-bacterial agents, or malodor protection.

The polymer system of the present invention also provides for a high loading of the functional ingredients while also providing these materials dispersed substantially uniformly throughout the polymeric system.

Figure 4:
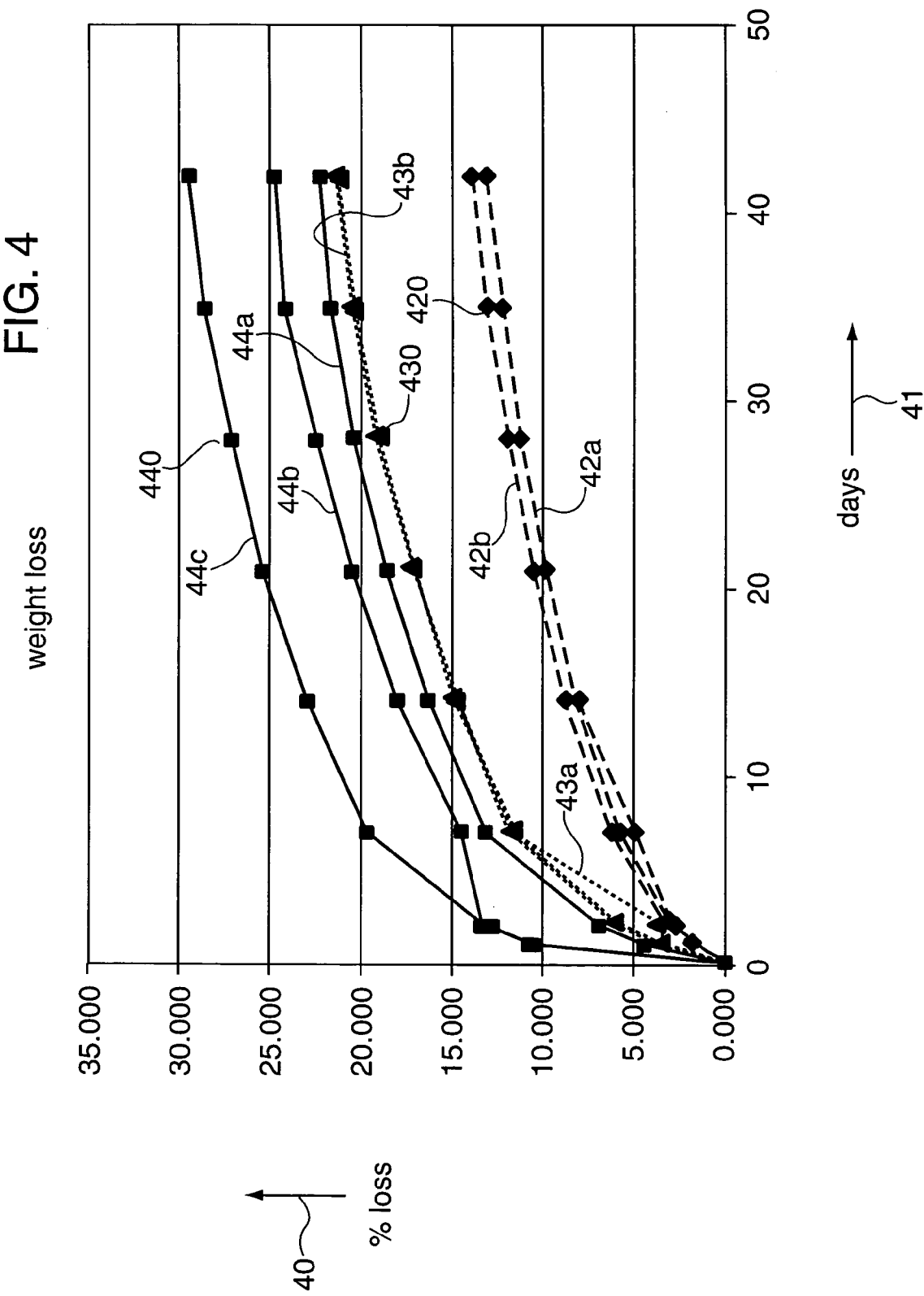
FIG. 4 is a graphical representation of a first series of curves for three different temperatures: 70° F., 110° F. and 120° F. showing time in days (on the 'x' axis) vs. % weight loss of fragrance A-containing stick article of our invention contained in the package as illustrated in FIG. 3. Fragrance A is described in Example A, infra. The stick article tested is that of Example IA, infra.

When carrying out such process, the percent weight loss, due to functional product loss, of stick article product per se, or product applied to an inanimate laminar surface, π vs. time, θ, measured in days, is according to the algorithm:

$$\pi = \alpha LN(\theta+1) + \beta$$

wherein α is a number in the range of from about 3.5 to about 7.5 and β is a number in the range of from about −1.0 to about +4.0 as more particularly described in the descriptions of FIGS. 4 and 5, infra. In the immediately-aforementioned algorithm, α is a function of absolute temperature as measured in degrees Rankine, T, and is according to the additional algorithm:

$$\alpha = 0.043 T - 18.96$$

and β is a function of absolute temperature as measured in degrees Rankine, T, and is according to the additional algorithm:

$$\beta = -0.6 LN(580 - T) + 1.7.$$

Referring to FIG. 1 and FIG. 2, the package 1 is adapted for use with a functional product containing stick and comprises a removable cap 2 for closing the package to protect the product therein. The cap is removed to permit application of the functional product, e.g., fragrance formulation to an inanimate solid laminar surface, e.g., a garbage bag or porcelain sink surface. The package 1 further comprises a barrel 3 containing the functional product-containing stick article 4 of our invention. The wall of the barrel 3 closely surrounds the stick article 4. An applicator 5 having an upwardly facing applicator surface 6 is formed integrally with the barrel 3 at the top end thereof. The lower end or bottom 8 of the stick 4 is supported within the package on an oval-shaped, movable support member 9 for movement up or down within the package relative to the barrel 3. A central portion of the movable support member 9 is provided with a threaded coupling sleeve 10 for cooperation with an elevator screw 11. The lower end of the elevator screw is axially fixed but rotatable within an opening in the closed, bottom end of the barrel 3. The elevator screw 11 includes a tapered section 13 which can be snap fitted within the opening using resilient tabs 20, in the bottom of the barrel 3 to retain the elevator screw 11 in the position shown in FIG. 2 while permitting the screw to be rotated by means of a knob 14 provided on the lower end of the screw. The bottom of the barrel 3 is dished inwardly to accommodate the knob 14 so that the package 1 can stand upright with the lower, outer, peripheral portion of the barrel, 3, resting on a flat supporting surface. Rotation of the knob 14 permits the user to raise or lower the movable support member 9 relative to the barrel 3 and thus raise and lower the functional product-containing stick article 4 of our invention relative to the barrel 3. The stick article 4 is shown in its lowered position in FIG. 2 with the top of the stick flush with the applicator surface 6. The several components of the package 1, including the cap 2, barrel 3, applicator 5 and coupling sleeve 10 are preferably each formed of plastic, e.g., polypropylene or high density polyethylene including talc-filled polypropylene using techniques well-known to those skilled in the art. The outer surface portion of the applicator surface 6 is rounded (curved downward) for reducing drag during application of the functional product contained in the stick article to the inanimate solid laminar surface being treated. The outer surface portion ends in free end 15, which is below the applicator surface edge adjacent the barrel. The outer surface portion part that downwardly extends to free end 15 of the applicator is a cooperating surface upon which the lower skirt 16 of the cap 2 can be slidably fitted and removed with slight resistance. The cap 2 can have ribs 27 associated therewith to maintain the cap in a proper position relative to the barrel 3.

Referring to FIG. 3, the functional product-containing stick article of our invention, 32, having application surface 33 is contained in package 30 which has a retaining wall 34 surrounding stick article 32. Holding wall 35, the purpose of which is to provide a convenient surface for an individual using package 30 in applying functional product from stick article 33 to an inanimate solid laminar surface, such as a garbage bag, garbage can; or toilet bowl surface, surrounds retaining wall 34 in close proximity thereto and is juxtaposed thereto. As the stick article 32 is used during application to the inanimate solid laminar surface, it is moved by the user upward past retaining wall 34 using the rotatable manual positioning knob 31 which rotates about the vertical axis of package 30 as the stick article 32 moves up and down relative to retainer wall 34.

Referring to FIG. 4 the % weight loss of the stick article of Example IA (with the stick article containing 30% fragrance of Example A, 67.5% UNICLEAR 100-LM, 2.0% sodium stearate and 0.5% CROMOLLIENT DP3-A) is measured along the "Y" (vertical) axis indicated by reference numeral 40, and time (in days) is measured along the "X" axis indicated by reference numeral 41. The curves on the graphical representation of FIG. 4 indicated by reference numerals 42a and 42b and the data point 420 are for measurements of weight loss % vs. time at 70° F. The curves on the graphical representation of FIG. 4 indicated by reference numerals 43a and 43b and the data point 430 are for measurements of weight loss % vs. time at 110° F. The curves on the graphical representation of FIG. 4 indicated by reference numerals 44a, 44b and 44c and the data point 440 are for measurements of weight loss % vs. time at 120° F. The following Table III sets forth the identifying reference numeral for each curve and the corresponding algorithm and standard error of estimate therefor:

TABLE III

| Reference Numeral | Algorithms (π = % weight loss; θ = time(days) | Standard error of the estimate |
|---|---|---|
| 42a | π = 3.53 LN (θ + 1) − 0.75 | 0.49 |
| 42b | π = 3.74 LN (θ + 1) − 0.73 | 0.49 |
| 43a | π = 5.68 LN (θ + 1) − 0.22 | 0.21 |
| 43b | π = 5.74 LN (θ + 1) − 0.26 | 0.23 |
| 44a | π = 5.96 LN (θ + 1) + 0.31 | 0.24 |
| 44b | π = 5.56 LN (θ + 1) + 3.95 | 2.03 |
| 44c | π = 7.16 LN (θ + 1) + 3.46 | 1.57 |

Referring to FIG. 5 the % weight loss of the stick article of Example IB (with the stick article containing 30% fragrance of Example B, 67.5% UNICLEAR 100-LM, 2.0% sodium stearate and 0.5% CROMOLLIENT DP3-A) is measured along the "Y" (vertical) axis indicated by reference numeral 50, and time (in days) is measured along the "X" axis indicated by reference numeral 51. The curves on the graphical representation of FIG. 5 indicated by reference numerals 52a, 52b and 52c and the data point 520 are for measurements of weight loss % vs. time at 70° F. The curves on the graphical representation of FIG. 5 indicated by reference numerals 53a and 53b and the data point 530 are for measurements of weight loss % vs. time at 110° F. The curves on the graphical representation of FIG. 5 indicated by reference numerals 54a, 54b and 54c and the data point 540 are for measurements of weight loss % vs. time at 120° F. The following Table IV sets forth the identifying reference numeral for each curve and the corresponding algorithm and standard error of estimate therefor:

TABLE IV

| Reference Numeral | Algorithms ($\pi$ = % weight loss; $\theta$ = time(days)) | Standard error of the estimate |
|---|---|---|
| 52a | $\pi = 4.14 \text{ LN}(\theta + 1) - 0.42$ | 0.39 |
| 52b | $\pi = 4.36 \text{ LN}(\theta + 1) - 0.38$ | 0.38 |
| 52c | $\pi = 4.52 \text{ LN}(\theta + 1) - 0.48$ | 0.40 |
| 53a | $\pi = 5.56 \text{ LN}(\theta + 1) + 0.33$ | 1.77 |
| 53b | $\pi = 5.79 \text{ LN}(\theta + 1) + 0.75$ | 0.59 |
| 54a | $\pi = 5.90 \text{ LN}(\theta + 1) + 0.19$ | 0.51 |
| 54b | $\pi = 6.10 \text{ LN}(\theta + 1) + 1.23$ | 0.81 |

All U.S. Patents and U.S. Published patent applications cited in this application are hereby incorporated by reference as if set forth in their entirely. The following examples are not meant to define or otherwise limit the scope of the invention. Rather the scope of the invention is to be ascertained according to the claims that follow the examples. Unless noted to the contrary, all percentages are given on a weight percent on a dry basis.

EXAMPLE A

The following fragrance composition was prepared:

| Fragrance Component | $\text{Clog}_{10}P$ value | Molecular Weight | Parts by Weight |
|---|---|---|---|
| ethyl undecylenate | 4.888 | 212.34 | 3.0 |
| geranyl anthranilate | 4.216 | 273.38 | 7.5 |
| α-irone | 3.820 | 206.33 | 6.3 |
| phenyl ethyl benzoate | 4.058 | 226.28 | 3.2 |
| d-limonene | 4.232 | 136.24 | 3.2 |
| cis-p-t-butylcyclohexyl acetate | 4.019 | 198.31 | 5.8 |
| amyl cinnamic aldehyde | 4.324 | 202.30 | 7.3 |
| benzaldehyde | 1.480 | 106.12 | 12.6 |
| benzyl acetate | 1.960 | 150.17 | 12.6 |

EXAMPLE B

The following fragrance was prepared:

| Fragrance Component | $\text{Clog}_{10}P$ value | Molecular Weight | Parts by Weight |
|---|---|---|---|
| ethyl undecylenate | 4.888 | 212.34 | 10.5 |
| geranyl anthranilate | 4.216 | 273.38 | 35.4 |
| α-irone | 3.820 | 206.33 | 5.3 |
| phenyl ethyl benzoate | 4.058 | 226.28 | 5.3 |
| phenylethyl phenyl acetate | 3.767 | 240.31 | 5.3 |
| 5-acetyl-1,1,2,3,3,6-hexamethyl indane | 5.977 | 258.41 | 2.5 |
| cyclopentadecanolide | 6.246 | 240.39 | 7.5 |
| d-limonene | 4.232 | 136.24 | 25.0 |
| cis-p-t-butylcyclohexyl acetate | 4.019 | 198.31 | 4.0 |
| amyl cinnamic aldehyde | 4.324 | 202.30 | 4.0 |
| benzaldehyde | 1.480 | 106.12 | 7.0 |
| benzyl acetate | 1.960 | 150.17 | 7.0 |
| laevo-carvone | 2.083 | 150.22 | 12.5 |
| geraniol | 2.649 | 154.26 | 25.0 |
| cis-jasmone | 2.712 | 164.25 | 3.0 |
| β-phenylethyl alcohol | 1.183 | 122.17 | 25.0 |

In each of the following Examples I–IV, fragrance formulation and compatible operativeness additive were premixed and added, with stirring to UNICLEAR-100-LM ester-terminated polyamide at a temperature of 40° C. The resulting mixture was then placed into molds designed to produce stick articles that fit into packages as illustrated in FIG. 3. The resulting packaged stick articles were then employed in coating fragrance-emitting films on garbage bags. The resulting value "V" (as defined supra) for each of the coatings is set forth in each of the examples; and is in the range of $7.5 \leq V \leq 10$.

EXAMPLE I

The following mixtures were prepared and molded into stick articles as set forth supra:

| | Parts by Weight | | | |
|---|---|---|---|---|
| Ingredient | Example IA | Example IB | Example IC | Example ID |
| Fragrance of example A, supra | 30.0 | 0 | 30.0 | 30.0 |
| Fragrance of Example B, supra | 0 | 30.0 | 0 | 0 |
| UNICLEAR 100-LM | 67.5 | 67.5 | 68.25 | 68.0 |
| Sodium Stearate | 2.0 | 2.0 | 1.25 | 1.50 |
| CROMOLLIENT DP3-A | 0.5 | 0.5 | 0.50 | 0.50 |

The "V" value of the resulting coatings for each of Examples IA, IB, IC and ID was 9.75.

EXAMPLE II

The following mixtures were prepared and molded into stick articles as set forth supra:

| | Parts by Weight | |
|---|---|---|
| Ingredient | Example IIA | Example IIB |
| Fragrance of example A, supra | 30.0 | 30.0 |
| UNICLEAR 100-LM | 69.50 | 69.75 |
| WICKENOL 163 | 0.5 | 0.25 |

The "V" value of the resulting coating for Example IIA was 7.75. The "V" value of the resulting coating for Example IIB was 8.10.

EXAMPLE III

The following mixtures were prepared and molded into stick articles as set forth supra:

| | Parts by Weight | |
|---|---|---|
| Ingredient | Example IIIA | Example IIIB |
| Fragrance of example B, supra | 30.0 | 30.0 |
| UNICLEAR 100-LM | 69.50 | 69.75 |
| CROMOLLIENT DP3-A | 0.5 | 0.25 |

The "V" value of the resulting coating for Example IIIA was 8.65. The "V" value of the resulting coating for Example IIIB was 8.35.

EXAMPLE IV

The following mixtures were prepared and molded into stick articles as set forth supra:

| Ingredient | Parts by Weight | | |
|---|---|---|---|
| | Example IVA | Example IVB | Example IVC |
| Fragrance of example A, supra | 30.0 | 30.0 | 30.0 |
| UNICLEAR 100-LM | 69.00 | 65.00 | 60.00 |
| TEGO Sorb Conc 50 | 1.00 | 5.00 | 10.00 |

The "V" value of the resulting coating for Example IVA was 8.75. The "V" value of the resulting coating for Example IVB was 8.90. The "V" value of the resulting coating for Example IVC was 9.10.

What is claimed is:

1. A substantially hydrocarbon-free functional substance-providing stick article having consistently-maintained functional composition and dimensional integrity comprising a stiff, monophasic, thermally-reversible composition comprising:
    (a) a structural support polymer selected from the group consisting of at least one ester-terminated polyamide and at least one tertiary amide-terminated polyamide;
    (b) a system-compatible functional composition selected from the group consisting of a perfume composition, an insect repellant composition, an animal repellant composition, an anti-microbial composition, an insect attractant composition and an air freshener composition; and
    (c) an operativeness additive wherein the operativeness additive is a mixture of octyl stearate, octyl palmitate and dioctyl adipate;
    with the provisos that the weight ratio range of structural support polymer: system-compatible functional composition is from about 90:10 to about 55:45 and the weight percent of operativeness additive is from about 0.2% to about 10% by weight of the functional substance-providing stick article.

2. The functional substance-providing stick article of claim 1 wherein the system-compatible functional composition is a perfume composition.

3. The functional substance-providing stick article of claim 1 wherein each component of the system-compatible functional composition has a $C \log_{10} P$ of between 1.0 and 6.5 wherein said $C \log_{10} P$ represents the calculated logarithm to the base 10 of the n-octanol/water partition coefficient of said component.

* * * * *